US00PP17007P3

(12) United States Plant Patent
Schubert

(10) Patent No.: US PP17,007 P3
(45) Date of Patent: Aug. 15, 2006

(54) BOXWOOD PLANT NAMED 'WEE WILLIE'

(50) Latin Name: *Buxus sinica var. insularis*
Varietal Denomination: Wee Willie

(76) Inventor: William E. Schubert, 2020 Route 307 E., Austinburg, OH (US) 44010

( * ) Notice: Subject to any disclaimer, the term of this patent is extended or adjusted under 35 U.S.C. 154(b) by 0 days.

(21) Appl. No.: 10/848,630

(22) Filed: May 20, 2004

(65) Prior Publication Data

US 2005/0262604 P1 Nov. 24, 2005

(51) Int. Cl.
*A01H 5/00* (2006.01)

(52) U.S. Cl. ..... Plt./226
(58) Field of Classification Search ..... Plt./226
See application file for complete search history.

(56) References Cited

U.S. PATENT DOCUMENTS

PP4,836 P 4/1982 Aldridge, Jr. ..... Plt./54
PP10,773 P 2/1999 Krasinsky et al. ..... Plt./54.1

*Primary Examiner*—Kent Bell
*Assistant Examiner*—June Hwu

(74) *Attorney, Agent, or Firm*—Wayne L. Lovercheck

(57) ABSTRACT

A new and distinct cultivar of boxwood that originated as a branch sport. The orderly arrangement of leaves on each stem gives this shrub considerable textural interest. This shrub displays excellent hardiness, and its emerald-green leaves retain their color through the winter. This semi-dwarf evergreen shrub displays an upright, dense growth habit, making it suitable for use in small gardens or as a low, formal hedge or border.

7 Drawing Sheets

*Buxus sinica* var. *insularis* 'Wee Willie'.

BRIEF SUMMARY OF THE INVENTION

The invention related to a new and distinct cultivar of boxwood, *Buxus sinica* var. *insularis* (synonym: *Buxus microphylla* var. *koreana*) that originated as a branch sport on the variety and was first observed in 1990, and was also asexually reproduced in Austinburg, Ohio. Rooted cuttings have been propagated by extracting cuttings from the current season's growth. The cuttings are taken in December and inserted into propagation media in flats. Rooted cuttings have been propaged by the inventor each year since 1990. The cultivar is distinguished by its decussate leaf arrangement, with successive pairs of leaves rotated 90 degrees on the stem axis from the previous pair. In this arrangement, its foliage resembles that of the box-leaved hebe, Hebe buxifolia, but we know of no other boxwood that displays this orderly leaf arrangement. Combined with the vertical orientation of the stems, the leaf arrangement gives a unique and attractive texture to this shrub.

The new cultivar is a dense-growing semi-dwarf broad-leaved evergreen, reaching a height and spread of 24 inches by 24 inches in six years from a rooted cutting. This cultivar is propagated from rooted cuttings, and plants propagated by this method consistently and uniformly display the unique characteristics of the original plant.

BRIEF DESCRIPTION OF THE PHOTOGRAPHS

DETAILED BOTANICAL DESCRIPTION

Figure 1:
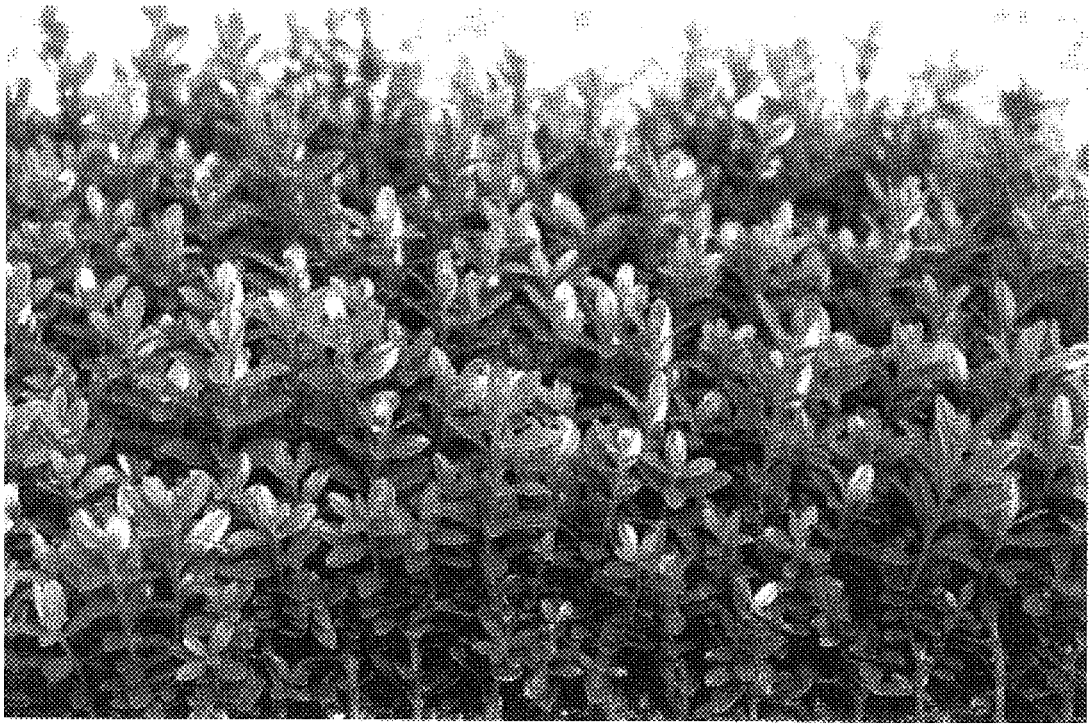
FIG. 1 shows propagation flat of rooted cuttings. Emerald green leaves with upright growth habit displaying pubescent stems. 1 year.
Figure 2:
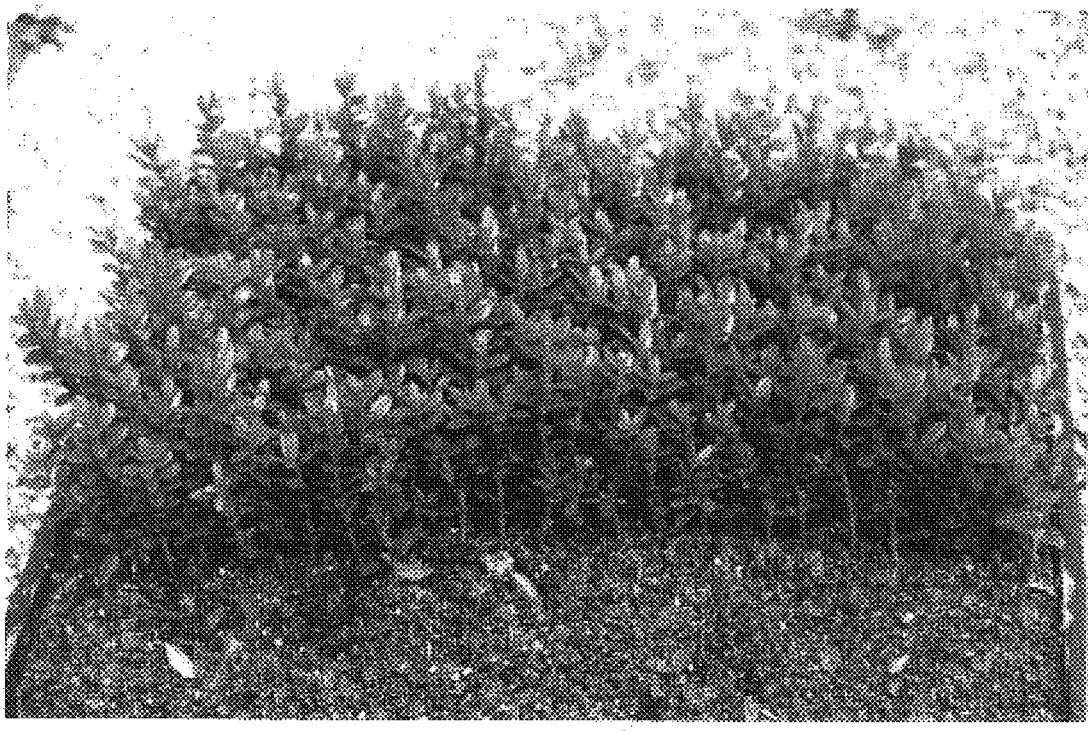
FIG. 2 shows propagation flat of rooted cuttings showing decussate arrangement of leaves on stems. 1 year.
Figure 3:
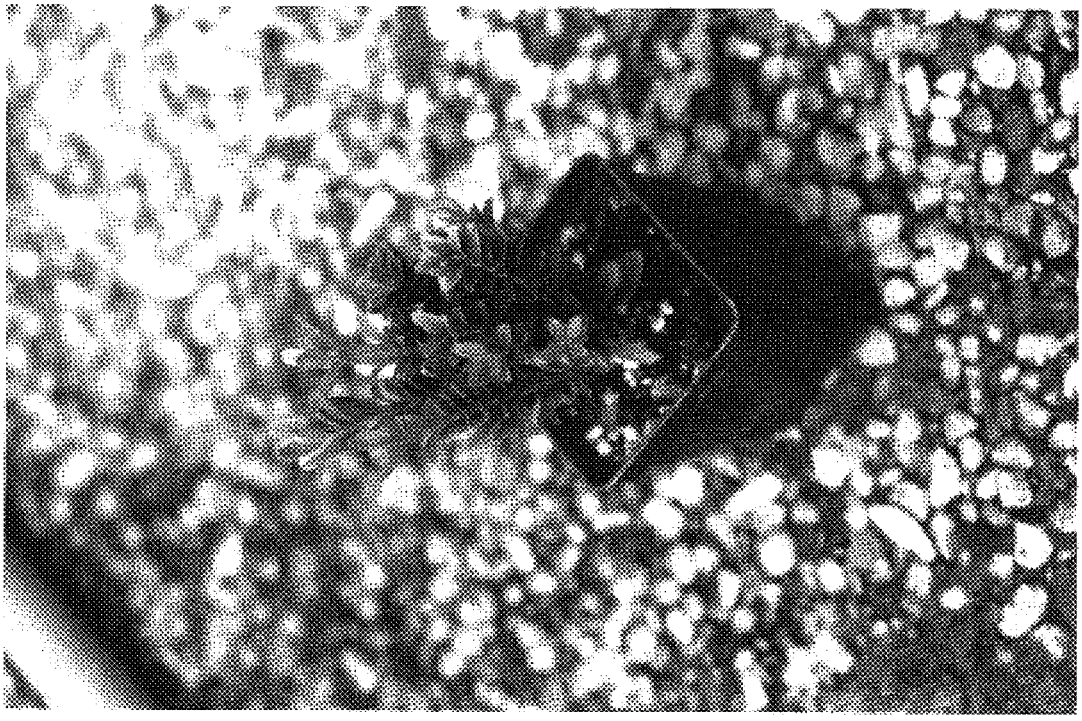
FIG. 3 shows rooted cutting in a 6.66 cm width by 8.89 cm height pot noting upright growth with dense compact habit. 2 year.
Figure 4:
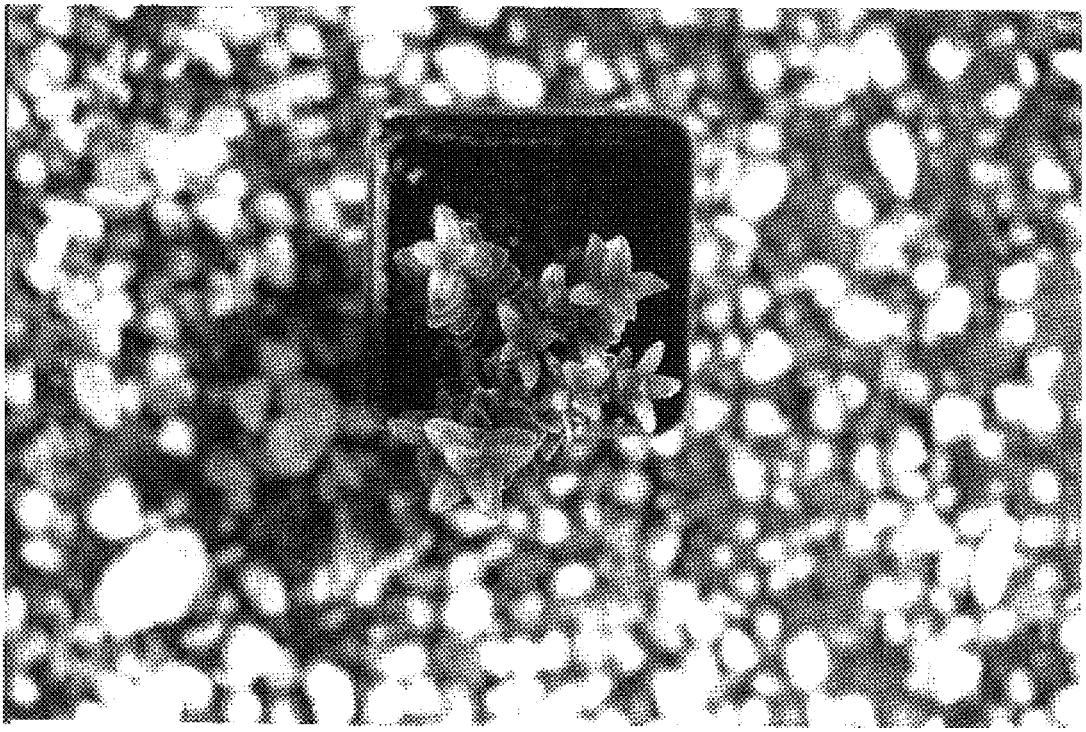
FIG. 4 shows rooted cutting in a 6.66 cm width by 8.89 cm height pot showing its successive pairs of leaves rotated 90 degrees on the stem axis from the previous pair. 2 year 4".
Figure 6:
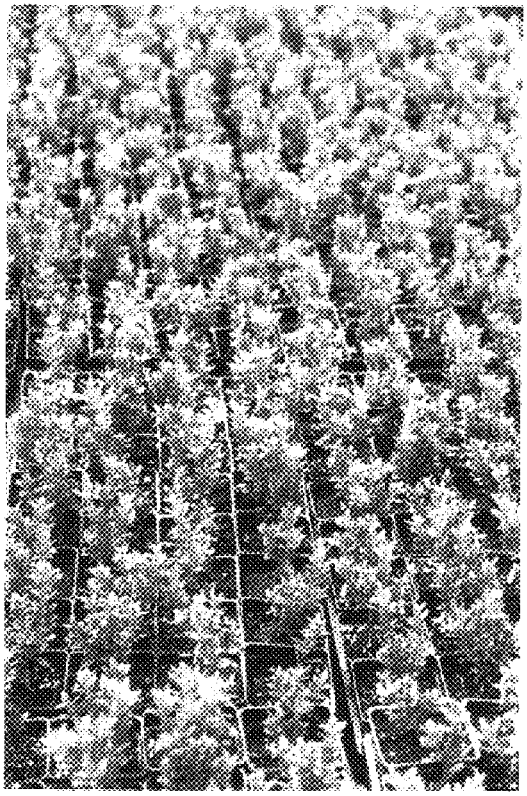
FIG. 6 shows rooted cutting displaying the consistent uniformity of the original plant. 2 year.
Figure 5:
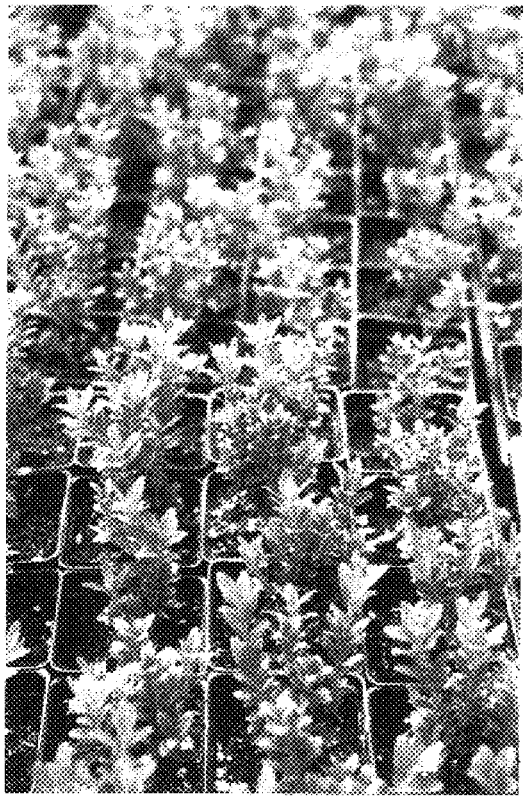
FIG. 5 shows rooted cutting displaying the consistent uniformity of the original plant. 2 year.
Figure 7:
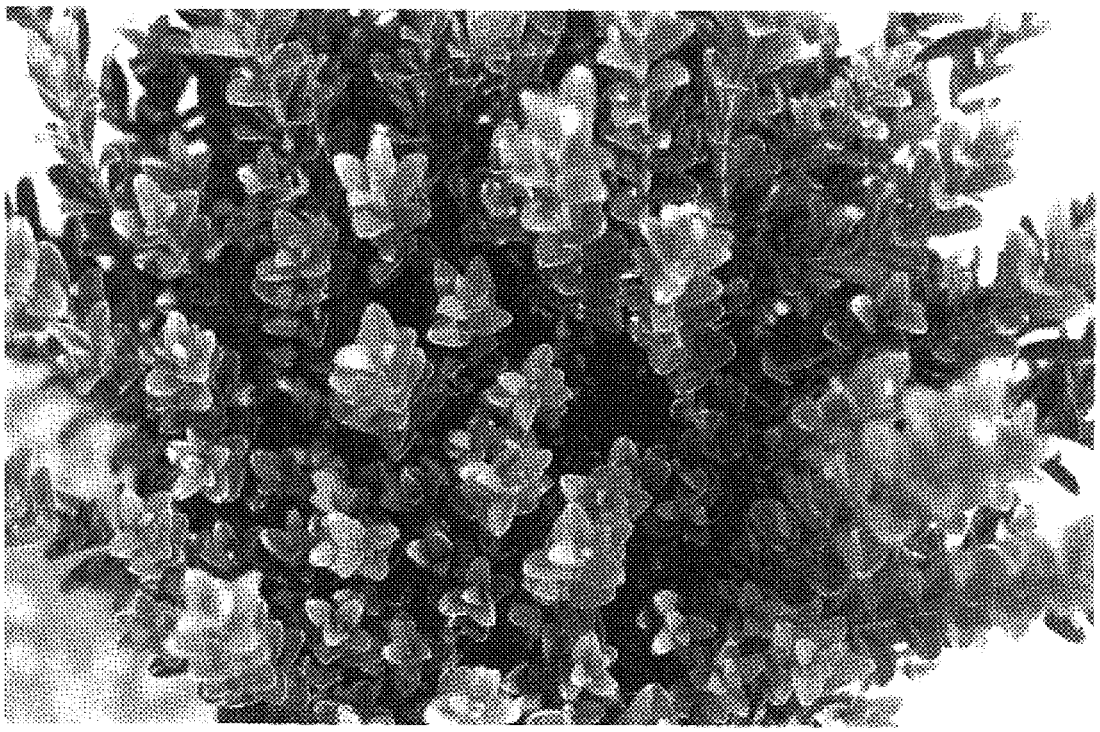
FIG. 7 shows finished material highlighting the rich emerald green color against its pubescent stems. 3 year 10"×12".
Figure 8:
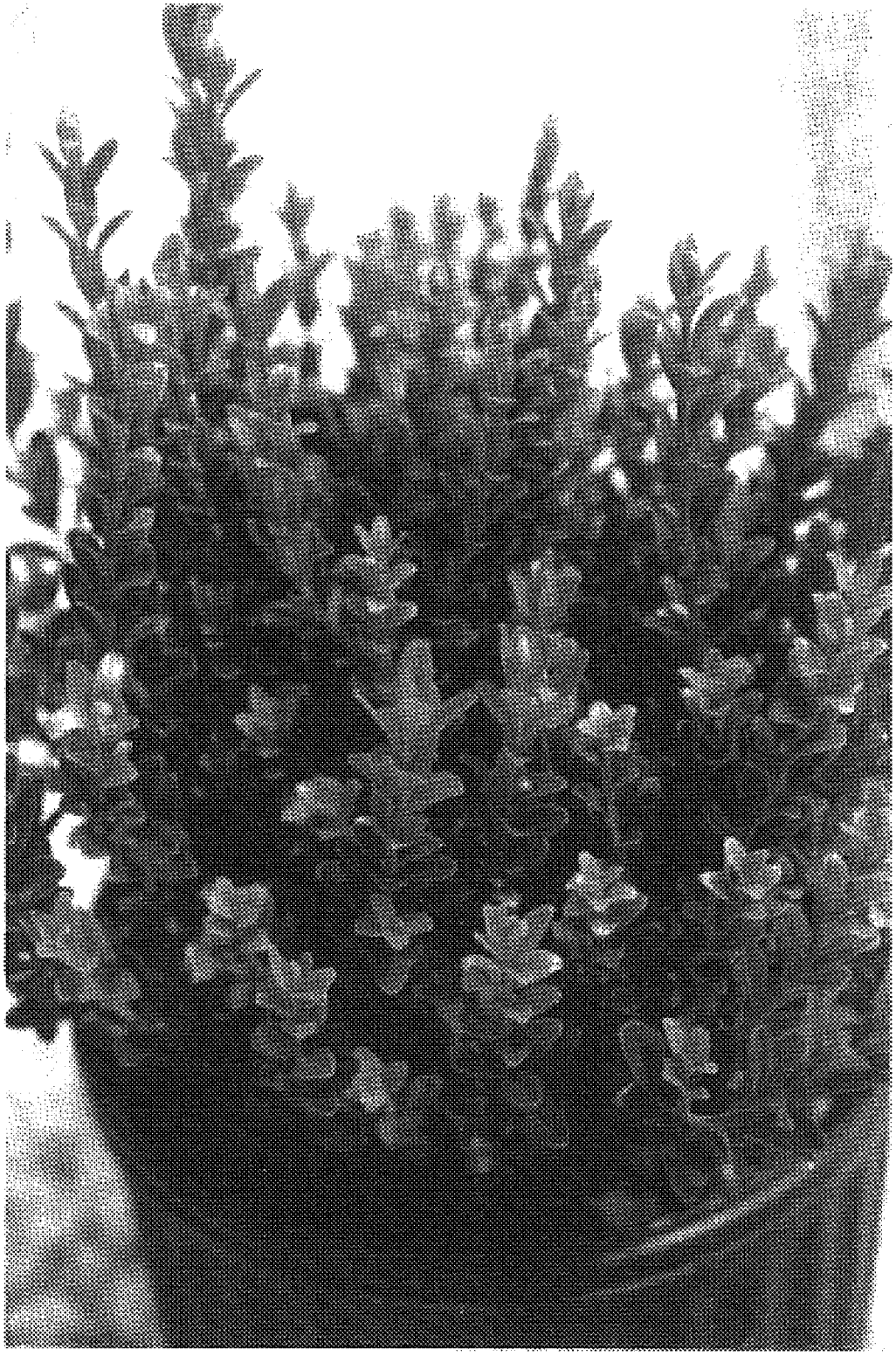
FIG. 8 shows finished material highlighting the rich emerald green color against its pubescent stems. 3 year 10"×12".
Figure 9:
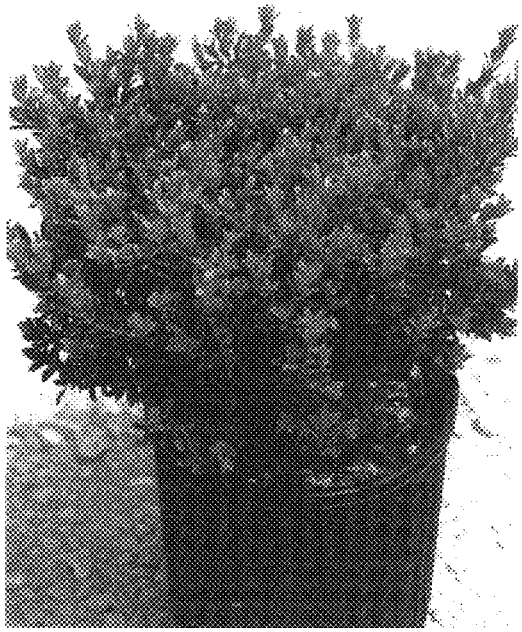
FIG. 9 shows finished material highlighting the rich emerald green color against its pubescent stems. 3 year 10"×12".
Figure 10:
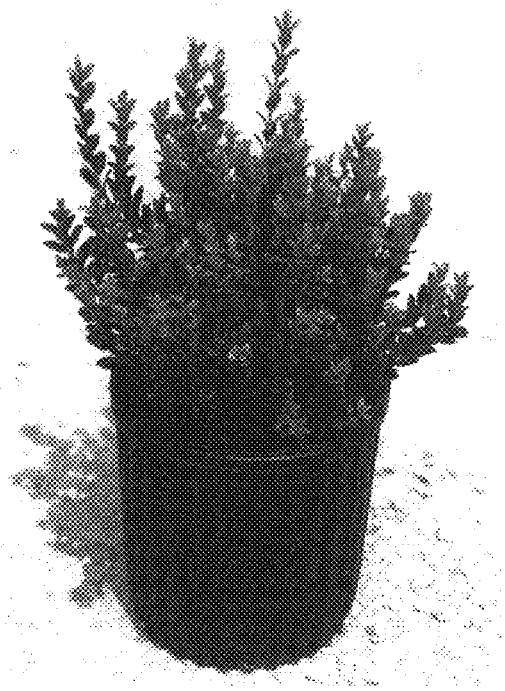
FIG. 10 shows specimen material. Extraordinary density and texture makes this shrub an excellent choice for small landscape or low formal hedge. 4 year 12"×15".
Figure 11:
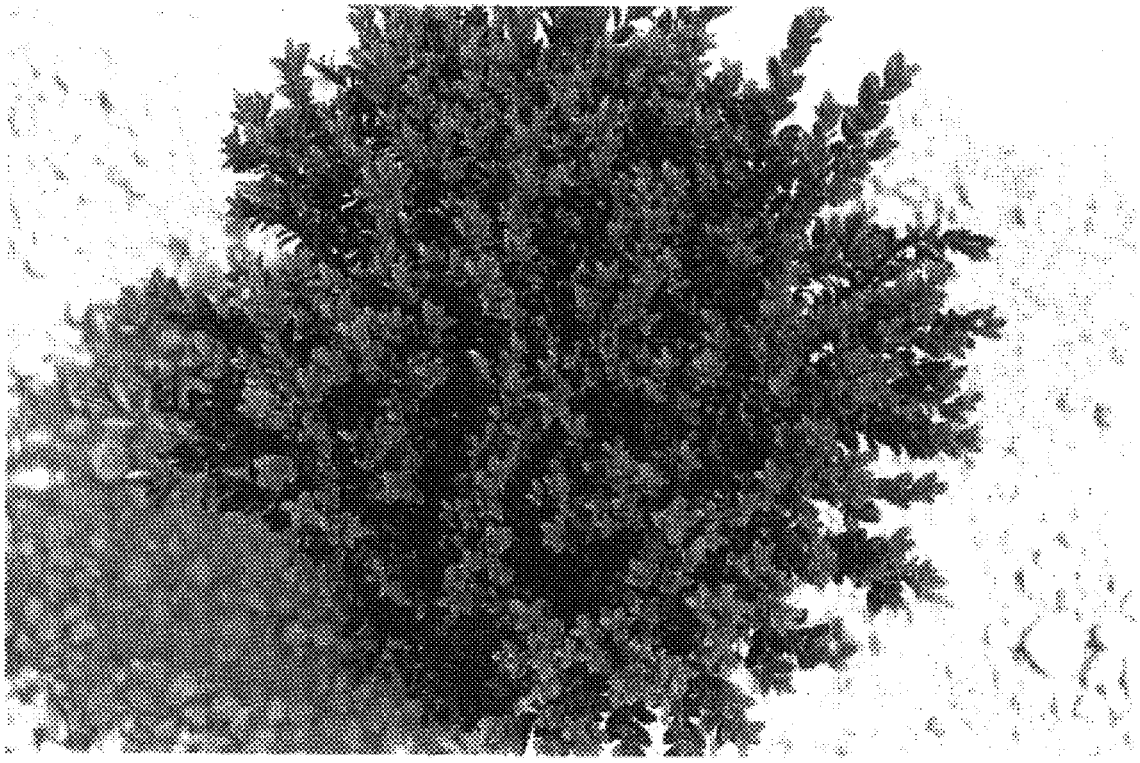
FIG. 11 shows specimen material. Extraordinary density and texture makes this shrub an excellent choice for small landscape or low formal hedge. 4 year 12"×15".
Figure 12:
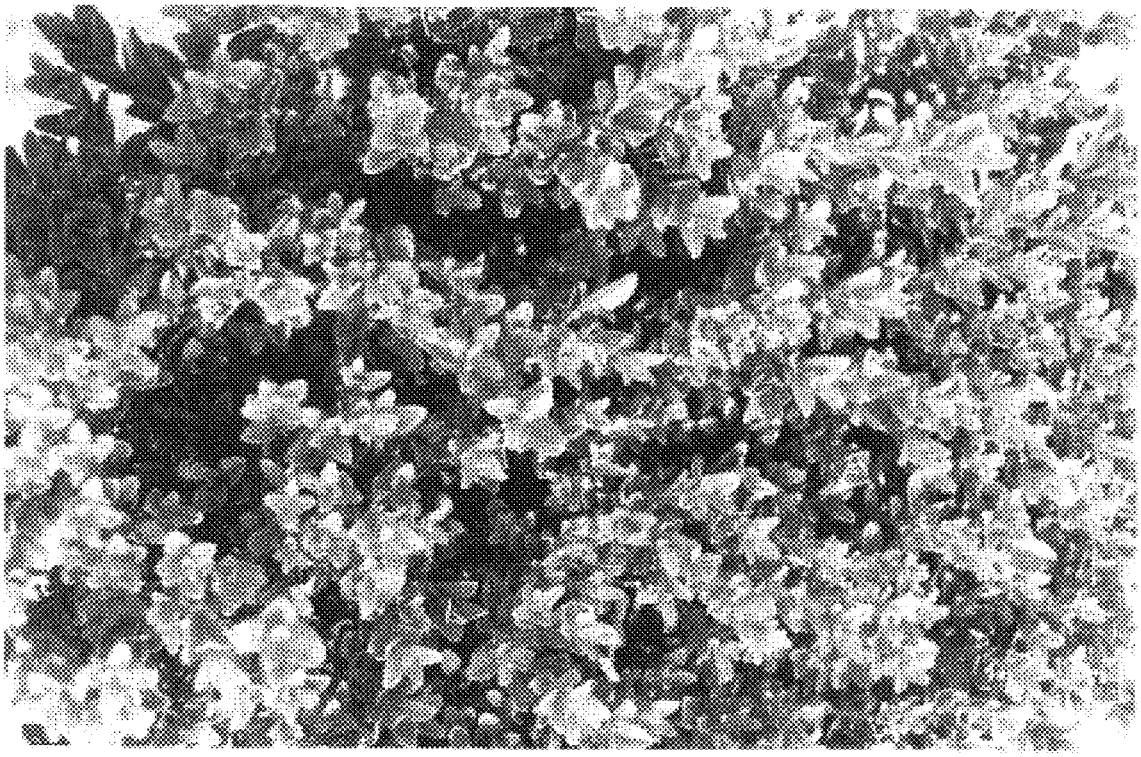
FIG. 12 shows specimen material. Extraordinary density and texture makes this shrub an excellent choice for small landscape or low formal hedge. 4 year 12"×15".

Parentage: Originated prior to 1990 as a branch sport on a specimen of *Buxus sinica* var. *insularis*.

Form/size: Compact shrub with upright branches, to two feet in height by two feet in spread in six years. Mature dimensions are expected to be consistent.

Hardiness: Fully hardy in USDA hardiness Zone 5. Probable hardiness in Zone 4. Has withstood minimum temperature of −20° F. without injury.

Growth rate: Slow, average of four inches per year.

Stems: Are four sided, Yellow-green Group 146B (Royal Horticultural Society Colour Chart 3rd Edition) the first year, tending to darken to Yellow-Green Group 152A, (Royal Horticultural Society Colour Chart 3rd Edition) from exposure to sun and age in the second year, as for the species. Young stems are pubescent. Mature stems are rounded with slightly corky ridges. Grey-yellow Group 161B (Royal Horticultural Society Colour Chart 3rd Edition). The petiole is glabrous and glossy, the underside is glabrous and glossy, except mid-vein extending to petiole is sparsely pubescent. Petiole color is Yellow-green Group 144A (Royal Horticultural Society Colour Chart 3rd Edition).

Leaves: Evergreen, lanceolate-elliptic with rounded apices and acute bases. Leaves borne in decussate arrangement on the stem. Leaf blades 1.5–2 cm. long and 0.7–1.0 cm wide at the widest point. Leaf stalks 0.1–0.2 cm in length. Sparse pubescence on the lower leaf surface on mid-vein, midrib and leaf stalk, the leaf blade otherwise glabrous and glossy on the upper surface. The color of the upper side of a mature leaf is Green Group 139A (Royal Horticultural Society Colour Chart 3rd Edition), and the color of the underside is Yellow-Green Group 146B. The leaf color is retained well through the winter.

Flowers: Not seen. Flowers are ornamentally insignificant in boxwood.

Fruits: Not produced so far. If produced, should not differ from the species.

Plant disease and pest resistance/susceptability: None observed.

Growth rate: When comparing 'Wee Willie' to normal little leaf boxwood, the internodel length between leaf pairs on current season's growth of 'Wee Willie' averages 0.8 to 1 cm as compared to normal little leaf boxwood at 1.8 to 2 cm. Also noted that on production plants (containerized) internodel length between leaf pairs is 0.8 to 1 cm. On landscape plants, internodel length is 30% closer.

Description: Newly opened leaves have a distinct color difference Yellow-green Group 144A (Royal Horticultural Society Colour Chart 3rd Edition) on upper surface, making it a very pleasant contrast. Lower surface of newly opened leaves are less glossy. Yellow-green Group 144A (Royal Horticultural Society Colour Chart 3rd Edition). Leaves are stacked and compressed in a decussate arrangement.

The new and distinct variety has been named the 'WEE WILLIE'.

I claim:

1. A new and distinct winter-hardy cultivar of *Buxus sinica* var. *insularis* plant, possessing the following characteristics:

a semi dwarf evergreen shrub with decussate leaf arrangement, providing a dense, compact shrub with unique and pleasing texture for use in small landscapes, masses and low hedges;

substantially as herein shown and described.

* * * * *